(12) United States Patent
Hamer et al.

(10) Patent No.: US 8,840,595 B2
(45) Date of Patent: *Sep. 23, 2014

(54) REMOVABLE SUCTION ASSEMBLY FOR MEDICAL HANDPIECES

(75) Inventors: James Hamer, Naples, FL (US); Philip O'Quinn, AveMaria, FL (US); Kenneth M. Adams, Naples, FL (US); Randall Hacker, Naples, FL (US)

(73) Assignee: Arthrex, Inc., Naples, FL (US)

( * ) Notice: Subject to any disclaimer, the term of this patent is extended or adjusted under 35 U.S.C. 154(b) by 498 days.

This patent is subject to a terminal disclaimer.

(21) Appl. No.: 12/561,866

(22) Filed: Sep. 17, 2009

(65) Prior Publication Data

US 2011/0065997 A1 Mar. 17, 2011

(51) Int. Cl.
  *A61M 1/00* (2006.01)
  *A61B 17/32* (2006.01)
  *A61B 17/00* (2006.01)
(52) U.S. Cl.
  CPC ........ *A61B 17/32002* (2013.01); *A61M 1/0041* (2013.01); *A61B 2017/00464* (2013.01)
  USPC ............................................. 604/319; 604/35
(58) Field of Classification Search
  USPC .................................................. 604/319, 35
  See application file for complete search history.

(56) References Cited

U.S. PATENT DOCUMENTS

| 4,541,457 | A | * | 9/1985 | Blenkush | 137/614.06 |
|---|---|---|---|---|---|
| 5,496,270 | A | * | 3/1996 | Nettekoven | 604/30 |
| 5,643,200 | A | * | 7/1997 | Edwards | 604/27 |
| 5,792,098 | A | * | 8/1998 | Felix et al. | 604/27 |
| 6,149,622 | A | * | 11/2000 | Marie | 604/43 |
| 6,312,441 | B1 | * | 11/2001 | Deng | 606/170 |
| 6,364,853 | B1 | * | 4/2002 | French et al. | 604/35 |
| 7,144,383 | B2 | * | 12/2006 | Arnett et al. | 604/35 |
| 7,153,296 | B2 | * | 12/2006 | Mitchell | 604/533 |
| 7,481,791 | B2 | * | 1/2009 | Cover et al. | 604/118 |
| 7,641,640 | B2 | * | 1/2010 | Burton et al. | 604/319 |
| 2004/0158203 | A1 | * | 8/2004 | Cover et al. | 604/118 |
| 2007/0106204 | A1 | * | 5/2007 | Fedenia et al. | 604/28 |
| 2008/0145816 | A1 | * | 6/2008 | Hershey et al. | 433/95 |
| 2009/0204065 | A1 | * | 8/2009 | Wright et al. | 604/35 |
| 2010/0016787 | A1 | * | 1/2010 | Shapiro et al. | 604/31 |
| 2011/0065997 | A1 | * | 3/2011 | Hamer et al. | 600/159 |
| 2011/0066122 | A1 | * | 3/2011 | Stanton et al. | 604/319 |
| 2011/0202023 | A1 | * | 8/2011 | Stanton et al. | 604/319 |

\* cited by examiner

*Primary Examiner* — Susan Su
*Assistant Examiner* — Guy K Townsend
(74) *Attorney, Agent, or Firm* — Dickstein Shapiro LLP

(57) ABSTRACT

Systems and methods provide for more efficient cleaning and sterilizing of surgical handpieces by using a removable valve assembly. The valve assembly is removable to provide access to a first suction passageway and a second suction passageway for cleaning purposes. The first suction passageway may also be removable.

16 Claims, 12 Drawing Sheets

REMOVABLE SUCTION ASSEMBLY FOR MEDICAL HANDPIECES

FIELD OF THE INVENTION

The present invention relates to systems and methods related to medical handpieces having suction passageways, and to rotating or other moving elements driven by a motor within the handpiece.

DESCRIPTION OF THE RELATED ART

Powered handpieces are commonly used in many medical specialities to drive surgical blades for performing various diverse cutting functions including resection, comminution, dissection, debridement, shaving, drilling, pulverizing and shaping of anatomical tissue. In arthroscopic surgery, powered or motorized handpieces and systems have been proposed as illustrated by the ADAPTEUR™ POWER (APSII) system of Arthrex, Inc. Naples, Fla.; Stryker CORE SHAVER SYSTEM of Stryker Endoscopy; and the ADVANTAGE System of Linvatec, Incorporated, Largo, Fla.

Conventional powered handpieces are typically all metal and reusable in design with permanently installed motors. Conventional powered handpieces generally use suction to evacuate anatomical tissue cut or excised by the blades or burrs. Powered handpieces currently in use generally force the excised anatomical tissue to follow a suction path which passes through the handpiece itself. Such handpieces are typically decontaminated and sterilized for reuse by steam autoclave and/or soaking in a disinfectant solution. The dissected tissue travels through portions of the suction passageways which reside within the handpiece. As a result, it is sometimes difficult to access the entire suction passageway during the cleaning and sterilization process to effectively remove tissue debris from within the suction passageways of the handpiece. Tissue debris left within the handpiece may result in contamination during the next surgical use of the handpiece.

BRIEF SUMMARY OF THE INVENTION

The present invention provides systems and methods for more efficient cleaning and sterilizing of surgical handpieces by using a removable valve assembly. The valve assembly is removably attached to a surgical handpiece and connects a first suction passageway to a second suction passageway. The valve assembly is removable to provide access to the first and second suction passageways for cleaning purposes. At least one of the first or second suction passageways may also be removable.

BRIEF DESCRIPTION OF THE DRAWINGS

The foregoing aspects and other aspects of this disclosure are described in detail below in connection with the accompanying drawing figures in which.

DETAILED DESCRIPTION OF THE PREFERRED EMBODIMENTS

The present invention provides systems and methods for more efficient cleaning and sterilizing of surgical handpieces by using a removable valve assembly. The valve assembly is removably attached to a surgical handpiece and connects a first suction passageway to a second suction passageway. The valve assembly is removable to provide access to the first and second suction passageways for cleaning purposes. At least one of the first or second suction passageways may also be removable.

The present invention also provides methods for efficient cleaning and sterilizing of surgical handpieces by using a removable valve assembly. According to an exemplary embodiment only, the method of the present invention comprises the steps of: (i) providing a surgical handpiece with a removable valve assembly connecting a first suction/aspiration passageway and a second suction/aspiration passageway in the proximity of a surgical site; (ii) conducting at least one surgical procedure involving removal of anatomical tissue from the surgical site; (iii) removing the valve assembly; and (iv) cleaning a portion of the first and second suction/aspiration passageways that were previously inaccessible, to remove tissue debris from the at least one of the first and second suction/aspiration passageways.

Figure 1:
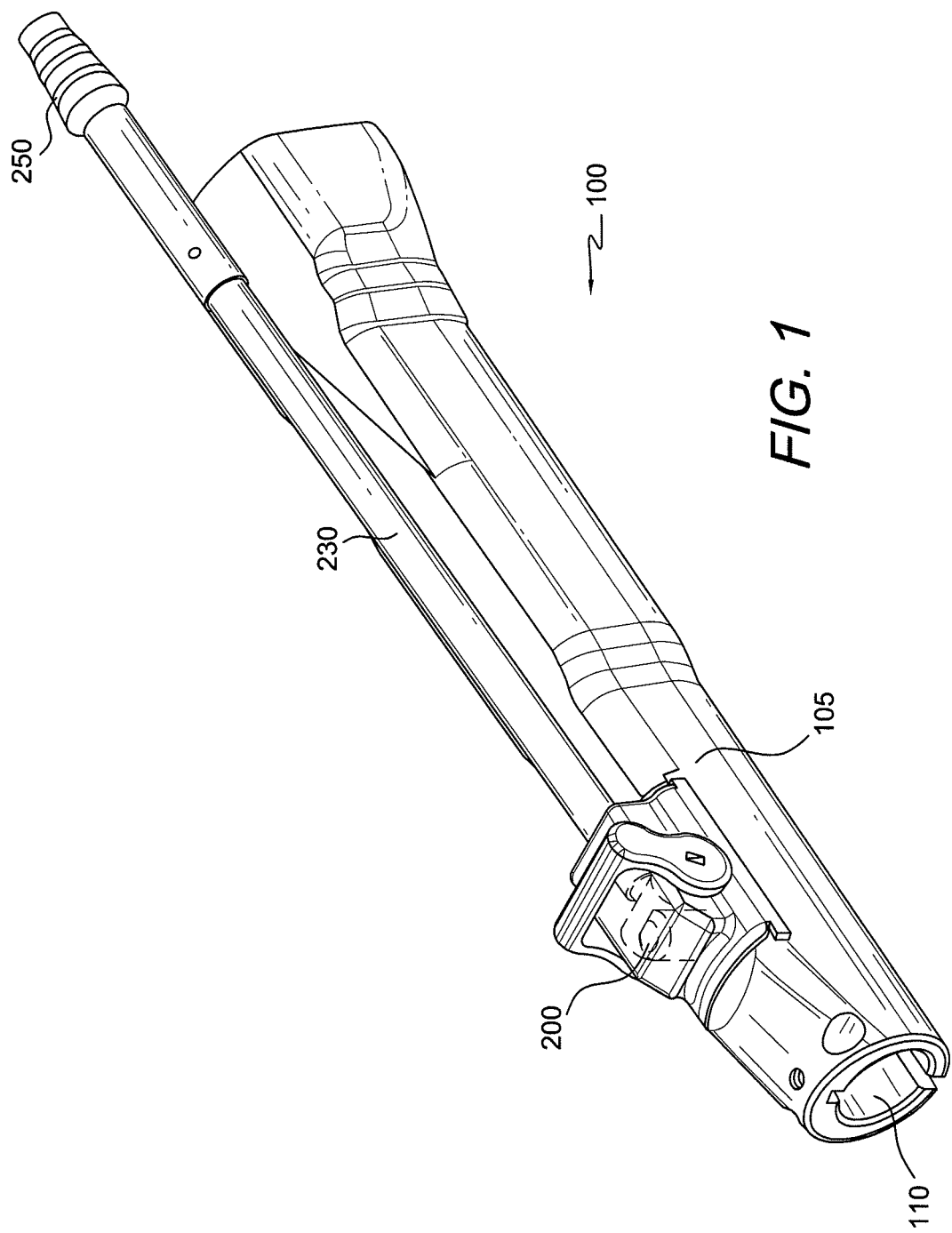
FIG. 1 is a perspective view of a powered handpiece according to an exemplary embodiment of the present invention.

Referring now to the drawings, where like elements are designated by like reference numerals, FIGS. 1-12 illustrate various structural elements of handpiece 100 of the present invention provided with valve assembly 200 and operatively connected to a surgical instrument 300. In an exemplary embodiment, and as shown in FIG. 1, handpiece 100 is a motorized, reusable surgical handpiece 100 (FIG. 1) configured to operate a variety of disposable (or reusable) surgical instruments. The handpiece 100 has a generally cylindrical shape and includes a housing 105. At its distal end, the handpiece 100 includes a cylindrical bore 110 for attachment of a surgical instrument. Located within the housing 105, a drive shaft 115 is coupled to a motor 120 also positioned within the handpiece 100. The handpiece may include a controlling means such as pushbuttons 125 and 135 or a foot control assembly, for example, that produces signals for use in controlling the motor.

The handpiece 100 is fully autoclavable. The handpiece 100 is preferably made of durable, medically acceptable materials, such as metal or plastic, including stainless steel, hard coat anodized aluminum, titanium, Ultem, PEEK, or Radel, capable of being sterilized to medical standards, such as by steam or flash autoclaving, gas sterilization and/or soaking in a disinfectant solution.

The handpiece 100 is employed in a surgical system that includes the handpiece, a console, a surgical instrument 300 (FIG. 2) or a set of surgical instruments, and optionally a foot control assembly. A processor positioned within the console controls the operating speed and direction of the motor of the handpiece 100. This, in turn, controls the operating speed and direction of the surgical instrument 300. For example, when the surgical instrument 300 includes an active portion 305 (such as a cutting blade or an abrading burr) that rotates about the longitudinal axis of the handpiece 100, the processor controls the direction and speed at which the active portion 305 rotates.

The processor controls the motor 120 in response to signals from the pushbuttons 125 and 135, the console, and/or the foot control assembly. The handpiece 100 is connected to the console by a cable that is attached to the proximal end of the handpiece.

Figure 2:
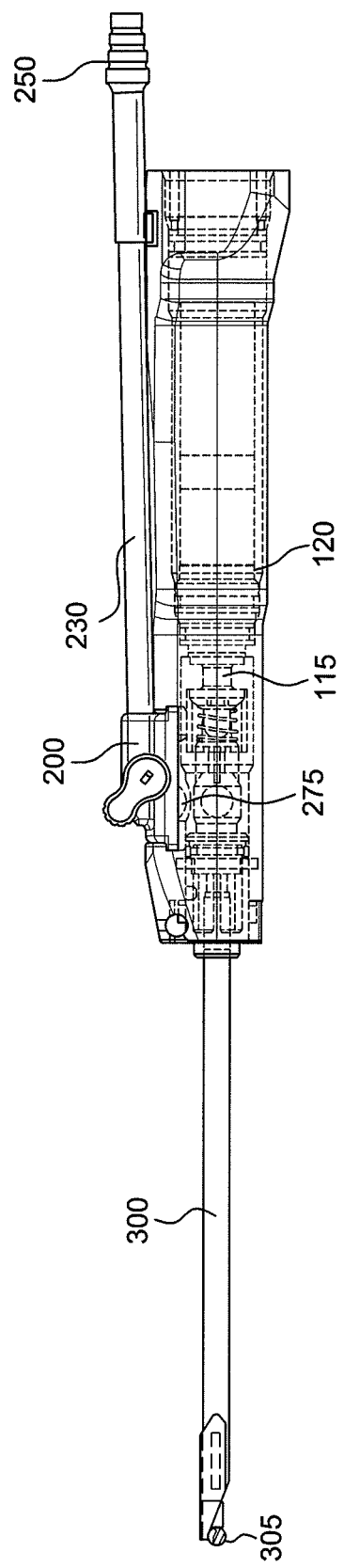
FIG. 2 is a side view of the powered handpiece of FIG. 1 (and with a surgical instrument attached to the powered handpiece)

A surgical instrument such as a shaver includes a drive shaft having an opening that permits material drawn through the inner tube of the surgical instrument to pass into the suction/aspiration passageway 230 of the handpiece 100. The suction/aspiration passageway 230 ends at barb connection 250 at the proximal end of the handpiece. During use, the barb connection 250 is connected to a source of suction (not shown). The handpiece 100 also includes a valve assembly 200 that controls flow through the suction/aspiration passageway 230. As shown in FIGS. 1 and 2, the valve assembly 200 is positioned on the handpiece near the distal end. In the open position, the valve assembly 200 allows fluid and material such as tissue debris to flow from the surgical instrument 300 through suction/aspiration passageway 275 created within bore 110 when the surgical instrument 300 is in place and the suction/aspiration passageway 230 of the handpiece 100. In the closed position, the valve assembly 200 stops the flow through the suction/aspiration passageway 230 and suction/aspiration passageway 275 from the surgical instrument through the handpiece.

At the end of a surgical procedure, the surgical instrument 300 (FIG. 2) is removed from the handpiece 100. The handpiece 100 is cleaned and sterilized for reuse. Tissue debris may be trapped along portions of the suction/aspiration passageways 275, 230. Accessing the entire suction/aspiration passageway to remove all tissue debris can be difficult. In the current invention, and as detailed in FIG. 3, for example, the valve assembly 200 is removable from the handpiece 100 and may also be disposable. By making the valve assembly 200 removable, it is possible to remove the portion of the suction/aspiration passageway that tends to accumulate the most tissue debris for thorough cleaning or disposal and replacement with a clean valve assembly. It also provides access to the inner, more remote portions of the suction/aspiration passageway that previously were either difficult to access or inaccessible. Removing the valve assembly 200 allows for direct access to suction/aspiration passageway 230 and opening 270 within the handpiece leading to bore 110 and suction/aspiration passageway 275. A brush, other cleaning instrument, or flushing instrument can be used through opening 270 to clean the suction/aspiration passageway 275 within bore 110 or through suction/aspiration passageway 230 and remove any remaining debris.

Figure 9:
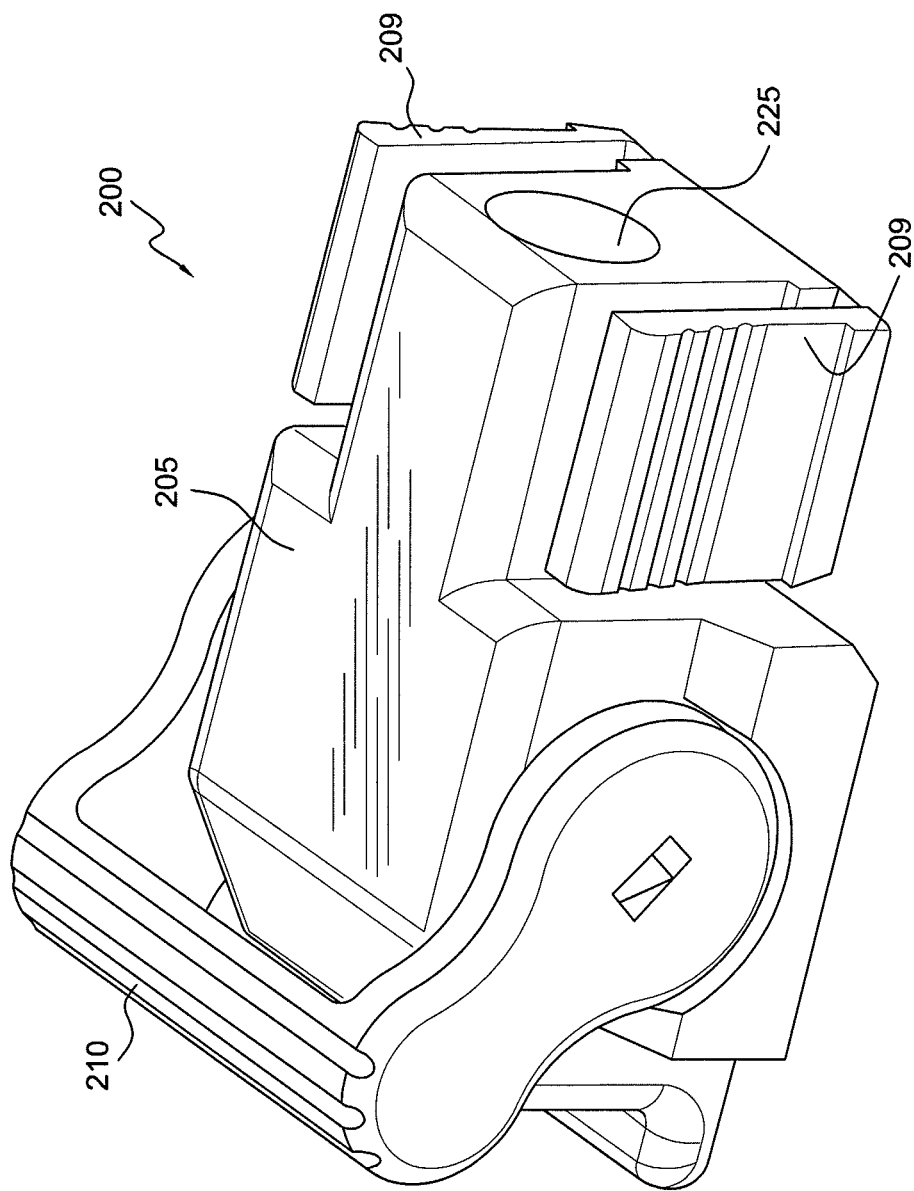
FIG. 9 illustrates an enlarged, perspective view of an embodiment of the removable suction valve assembly according to the present invention.
Figure 10:
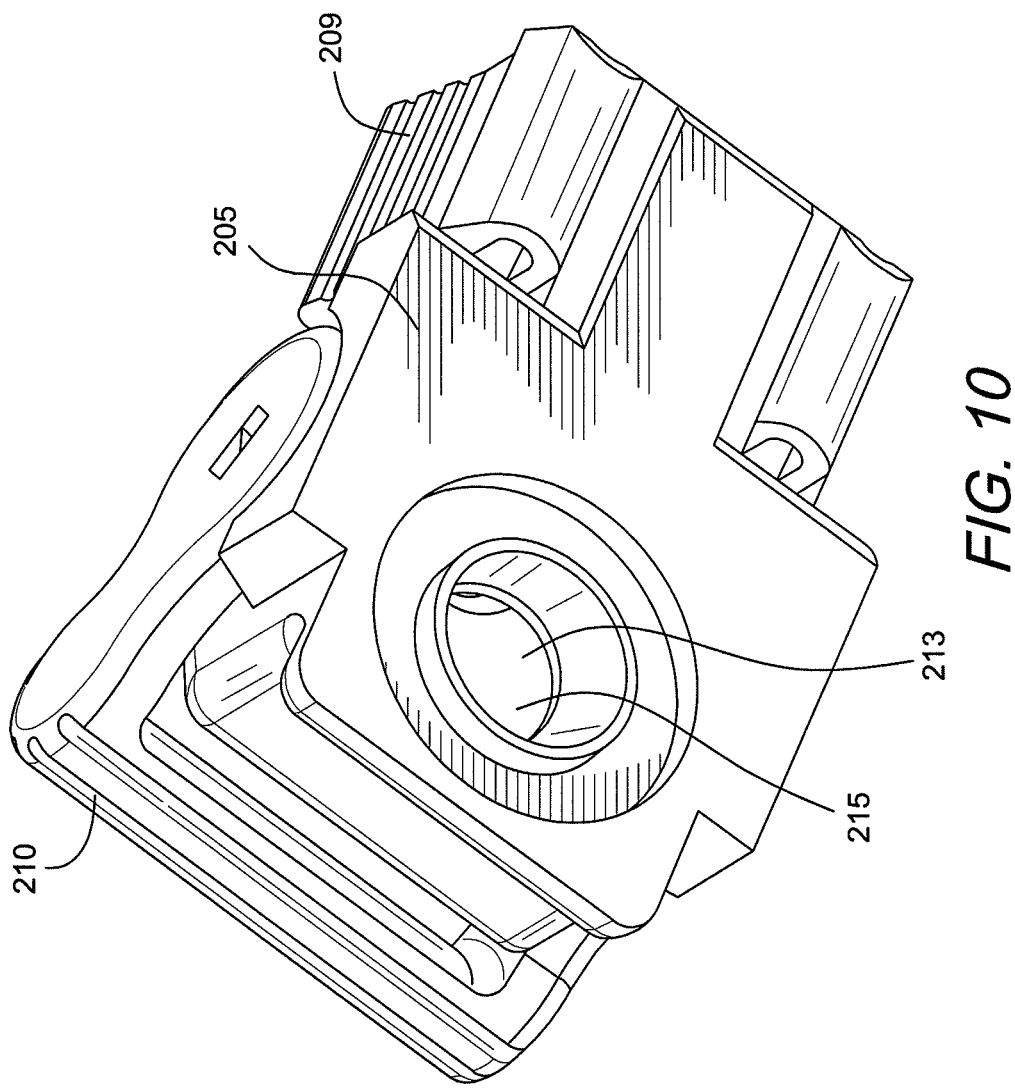
FIG. 10 illustrates a bottom view of the removable suction valve assembly of FIG. 9.

Details of the valve assembly 200 are illustrated in FIGS. 9 and 10. Body 205 of the valve assembly 200 has a lever 210 for opening and closing the barrel/valve 215 to allow or prevent flow through the suction/aspiration passageway 230 of the handpiece 100. Body 205 has an opening 213 (FIG. 10) for communicating with the suction/aspiration passageway 275 within bore 110 leading from the surgical instrument. Body 205 also has an opening 225 (FIG. 9) communicating with the suction/aspiration passageway 230 leading from the handpiece. Body 205 is removable from the handpiece 100 allowing access to portions of the suction/aspiration passageway. In an exemplary embodiment shown in FIGS. 1 and 3, valve assembly 200 may slidingly engage the handpiece in a unidirectional manner having stops 207 to prevent the valve assembly from sliding completely out of the handpiece. In an alternate embodiment, shown in FIGS. 9 and 10, the valve assembly may be removable from the handpiece using a snap-fit connection with push-in tabs 209. The valve assembly may be removable in any number of ways known to one skilled in the art including a twist-in fashion. The valve assembly may be made from plastic or metal materials, such as stainless steel, aluminum or injection moldable materials like polycarbonate, ultem, PEEK, Radel or ABS.

Figure 3:
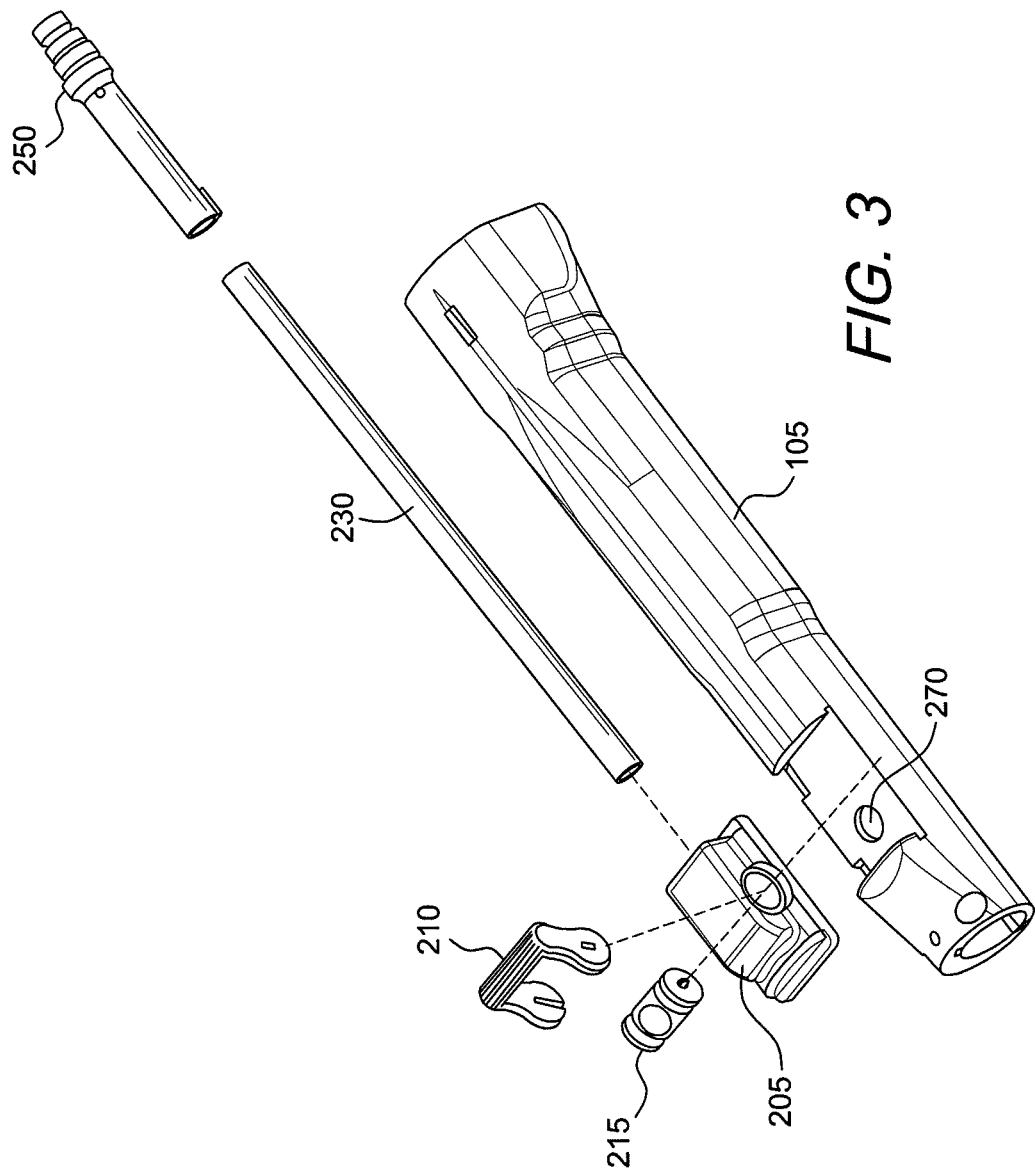
FIG. 3 is an exploded view of the powered handpiece of FIG. 1.
Figure 4:
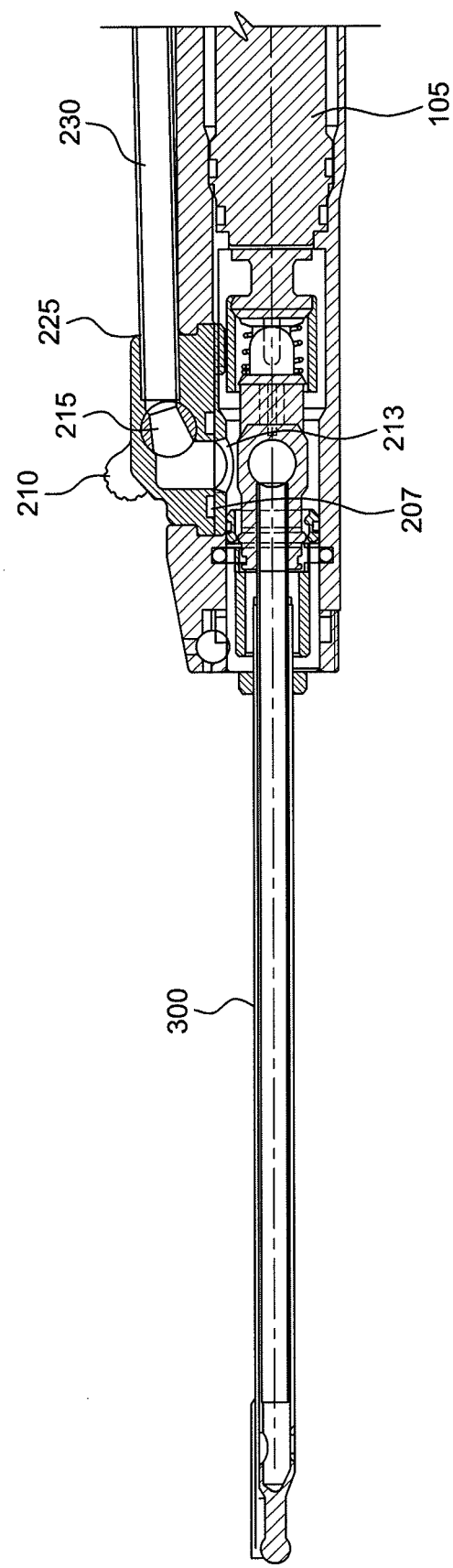
FIG. 4 is a sectional view of the powered handpiece/surgical instrument of FIG. 2, with the suction valve assembly in the open position.
Figure 5:
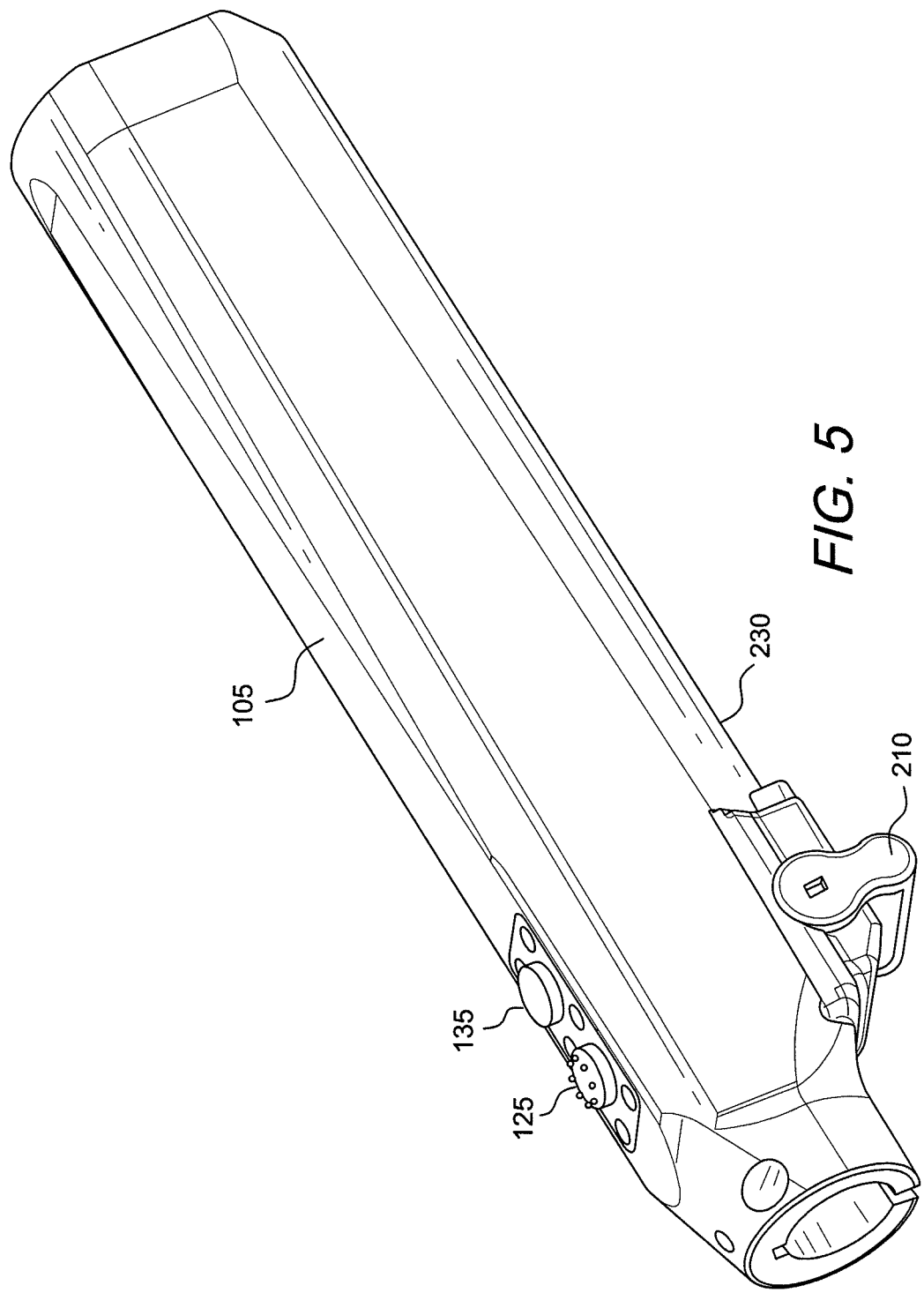
FIG. 5 illustrates a perspective view of another exemplary embodiment of a powered handpiece of the present invention, having pushbutton controls and an internal suction passageway.
Figure 6:
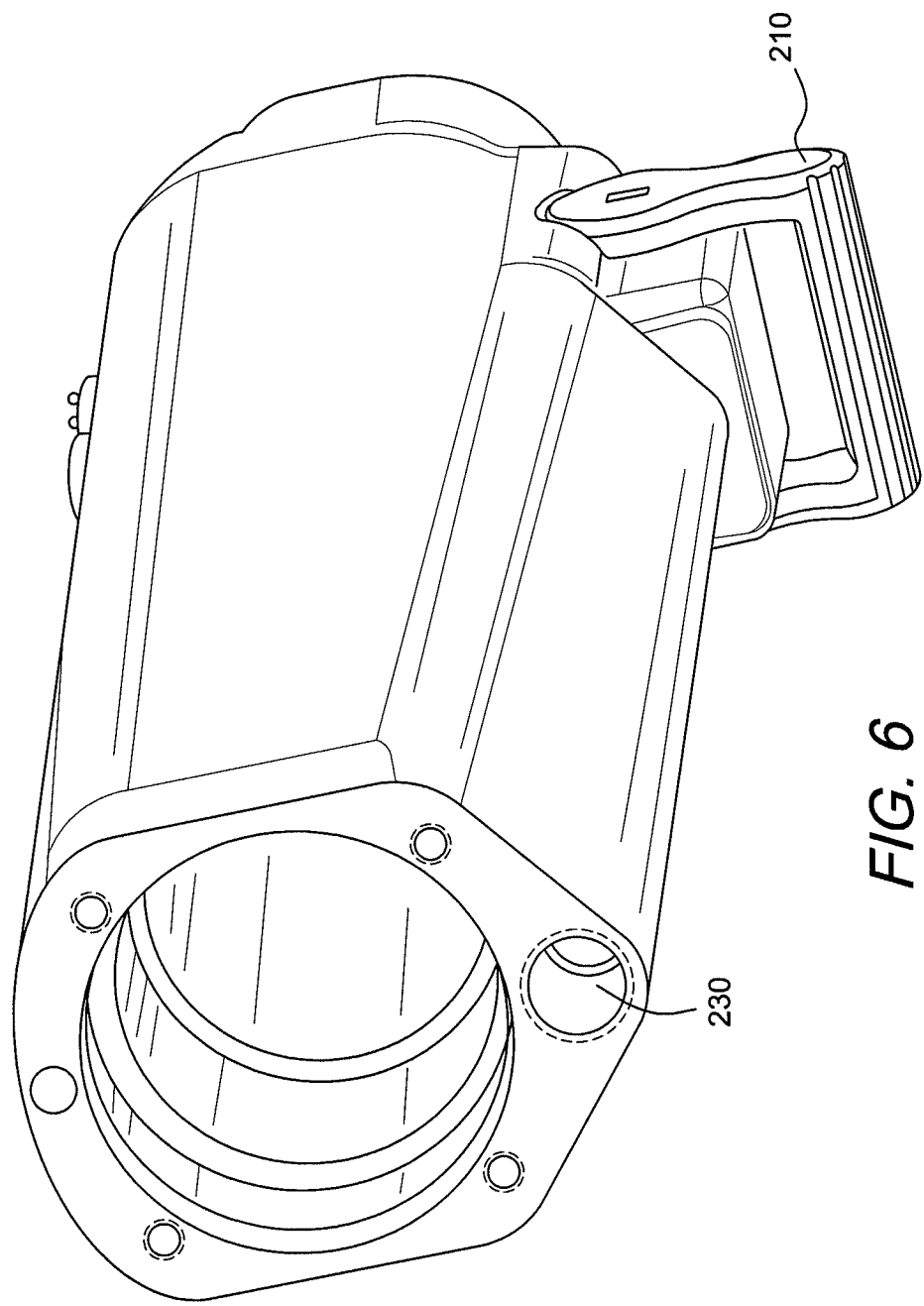
FIG. 6 illustrates a perspective view from the proximal end of the powered handpiece of FIG. 5.
Figure 7:
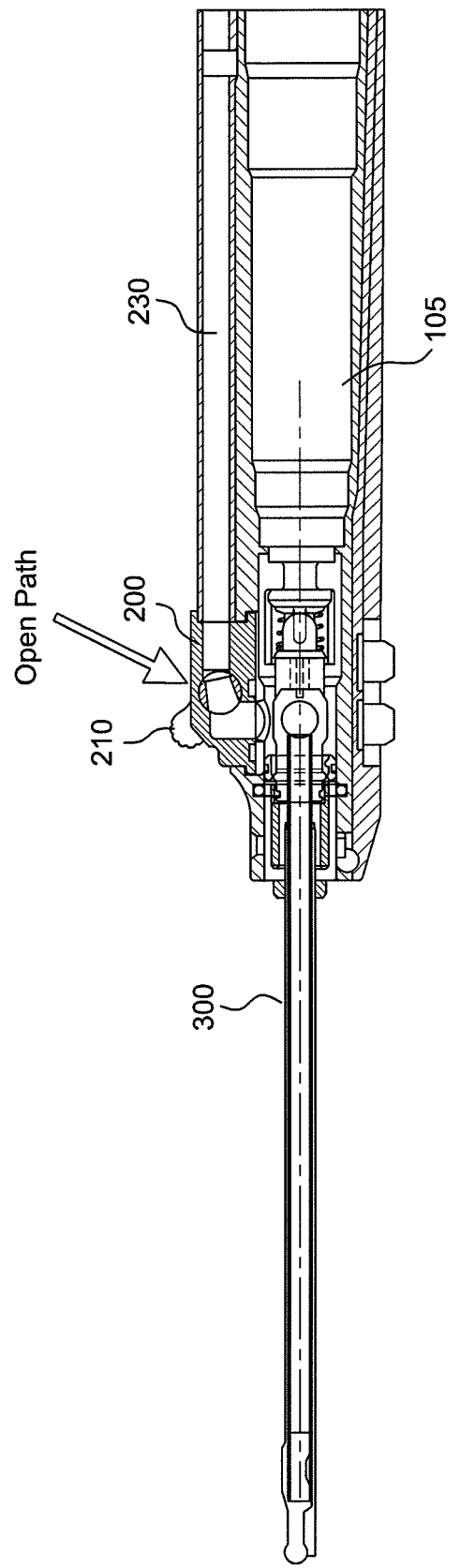
FIG. 7 illustrates a sectional view of the handpiece in FIG. 5 (with a surgical instrument attached to the powered handpiece), and with the valve assembly in an open position.
Figure 8:
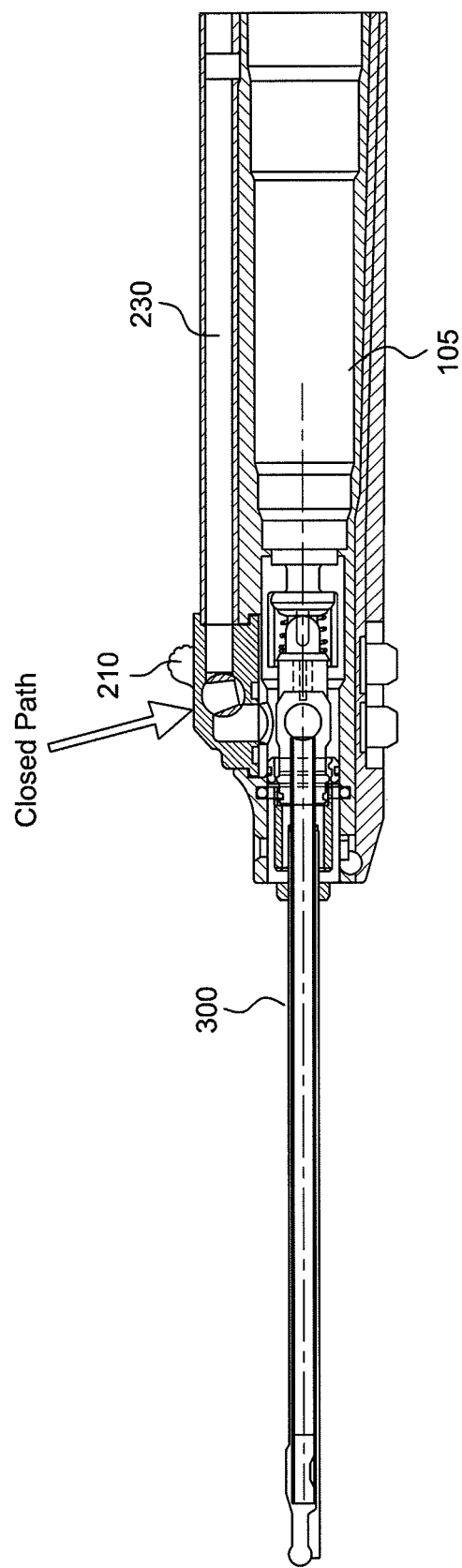
FIG. 8 illustrates a sectional view of the handpiece of FIG. 5 (with a surgical instrument attached to the powered handpiece), and with the suction valve assembly in a closed position.

In addition to the valve assembly being removable, the suction/aspiration passageway 230 could also be removable and disposable. As shown in FIGS. 1 and 3, the suction/aspiration passageway is external to the handpiece and may be removable for cleaning of the remaining portions of the suction/aspiration passageway. Preferably, the removable portion of the suction/aspiration passageway would be connected to the valve assembly such that both the valve assembly and the portion of the suction/aspiration passageway would be removable as one piece. The removable portion of the aspiration passageway may be manufactured from plastic or metal materials such as stainless steel, aluminum, PEEK, radel, ultem.

In some models of handpieces, the suction/aspiration passageway is an integral portion of the handpiece housing 105 as shown in FIGS. 5-8. The suction/aspiration passageway 230 is formed within the housing of the handpiece, extending from a proximal end to a distal end. The removable valve assembly 200 functions the same way to provide access to the suction/aspiration passageway for cleaning.

Figure 11:
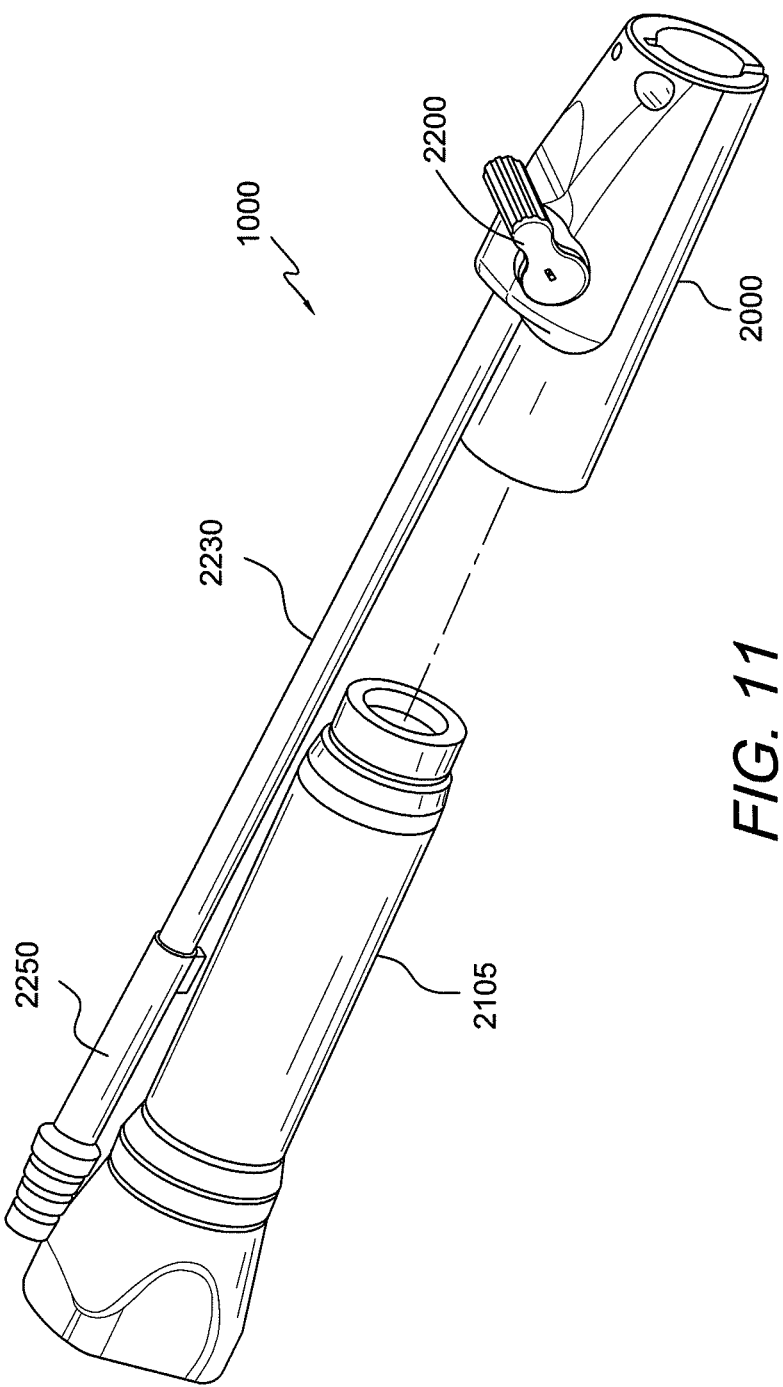
FIGS. 11 and 12 illustrate an alternate embodiment of a handpiece having a removable collet with a suction valve.
Figure 12:
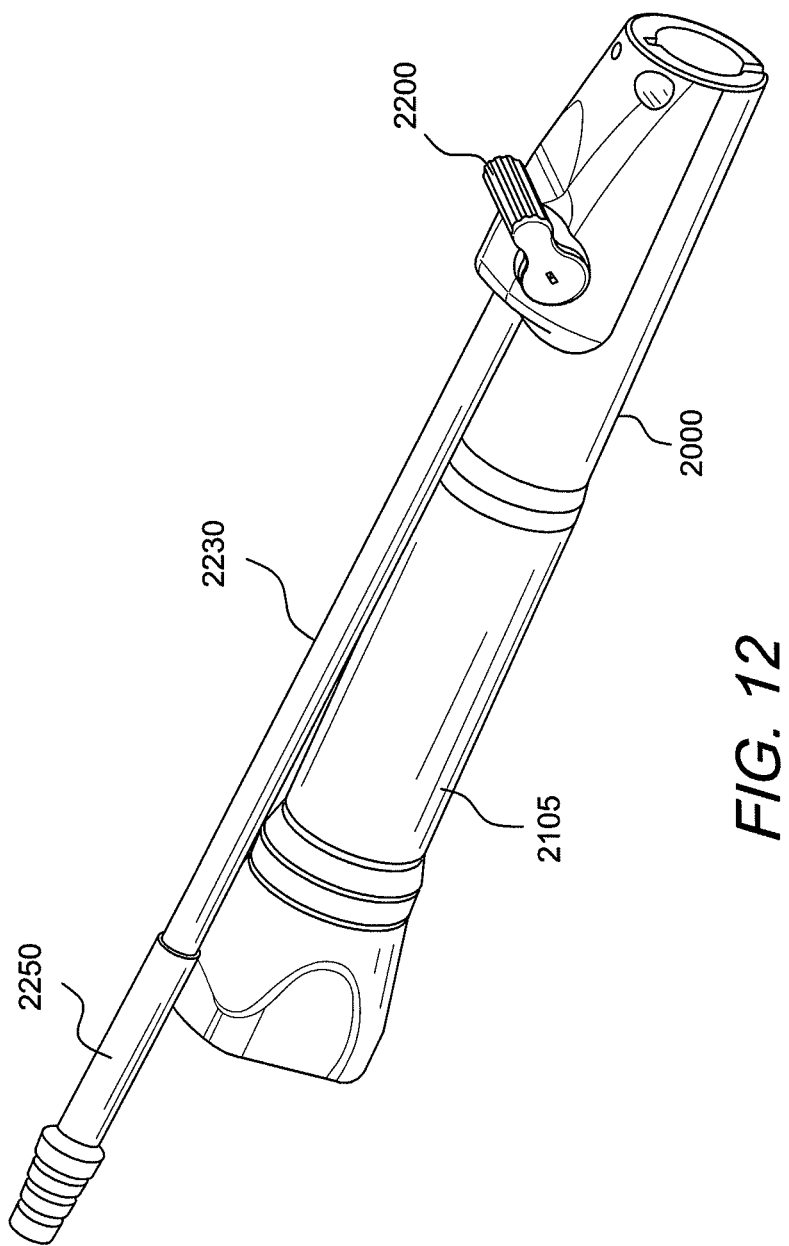

In an alternate embodiment, the entire distal end of the handpiece may be removable for cleaning. This embodiment would be more preferable in the foot control handpiece as the electrical communication portion resides in the foot control rather than the handpiece itself. As shown in FIGS. 11 and 12, surgical handpiece 1000 includes a removable collet assembly 2000 having a suction valve assembly 2200, a housing 2105, a suction/aspiration passageway 2230 and a barb connector 2250. The collet assembly 2000 may be removable in any number of ways known to one skilled in the art such as threading, snap fit, or quick connect coupling. The suction valve assembly 2200 connects the first suction/aspiration passageway 2230 to the second suction/aspiration passageway of the surgical instrument. The suction valve assembly 2200 works the same as suction valve 200 to open and close the suction/aspiration passageway. The removable collet 2000 may be disposed of after use to prevent any tissue debris from remaining within the handpiece and a new clean collet may be provided for additional use of the handpiece. The first suction/aspiration passageway may also be removable and disposable to prevent tissue debris from remaining during additional use of the handpiece.

The handpiece of the present invention may be used in many different surgical areas including, but not limited to, arthroscopy, laproscopy, maxillo-facial dental and cranial applications.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A surgical handpiece, comprising:
a first suction passageway;
a second suction passageway; and
a removable valve assembly connecting the first suction passageway to the second suction passageway, the removable valve assembly being removably attached to the handpiece, the removable valve assembly comprising a body including an opening communicating with the first and second suction passageways, a lever for opening and closing a valve, and push-in tabs for a snap-fit connection, the removable valve assembly being removable in one piece to provide direct access to the first and second suction passageways for cleaning purposes and removing tissue debris, wherein the removable valve assembly is removably attached to, and detached from, the handpiece using the snap-fit connection with push-in tabs to allow the body of the valve assembly to snap-fit to the handpiece.

2. The surgical handpiece of claim 1, wherein the first suction passageway is removable from the handpiece.

3. The surgical handpiece of claim 1, wherein the valve assembly is slidingly engaged with the handpiece.

4. The surgical handpiece of claim 1, wherein the first suction passageway is integral to the handpiece.

5. The surgical handpiece of claim 1, wherein the valve assembly is disposable.

6. A method for cleaning a surgical handpiece, comprising:
removing a valve assembly connecting a first suction passageway and a second suction passageway from the surgical handpiece, the valve assembly being removably attached to the handpiece, the valve assembly being removable in one piece, the valve assembly comprising a body including an opening communicating with the first and second suction passageways, a lever for opening and closing a valve, and push-in tabs for a snap-fit connection of the body to the handpiece; and
directly accessing a portion of at least one of the first and second suction passageways being inaccessible when said valve assembly is attached to the handpiece; and cleaning said portion after removing the valve assembly from the handpiece.

7. The method of claim 6, further comprising:
removing the first suction passageway; and
disposing of the first suction passageway.

8. The method of claim 6, further comprising the step of cleaning a portion of the second suction passageway.

9. The method of claim 6, further comprising the step of replacing the valve assembly.

10. A surgical handpiece, comprising:
a shaft;
a first suction/aspiration passageway attached to the shaft and connected to a source of suction;
a second suction/aspiration passageway provided within the shaft and connected to a surgical instrument; and
a valve assembly removably attached to the shaft by being snap-fitted to the handpiece, the valve assembly being configured to connect the first suction/aspiration passageway and the second suction/aspiration passageway, the valve assembly being removable in one piece, the valve assembly comprising a body including an opening communicating with the first and second suction/aspiration passageways, a lever for opening and closing a valve, and push-in tabs for the snap-fit connection.

11. The surgical handpiece of claim 10, wherein the first suction/aspiration passageway is removable from the handpiece.

12. The surgical handpiece of claim 10, wherein the valve assembly is disposable.

13. The surgical handpiece of claim 10, wherein the surgical instrument is a shaver, abrader, resector, scissor, forceps, tissue retractor or electrode.

14. The surgical handpiece of claim 10, wherein the surgical instrument comprises a cutting blade or an abrading burr.

15. The surgical handpiece of claim 10, wherein the surgical instrument is an electrosurgical instrument.

16. The surgical handpiece of claim 10, wherein the surgical instrument is an arthroscopic or endoscopic instrument.

* * * * *